(12) United States Patent
Merten et al.

(10) Patent No.: US 10,569,272 B2
(45) Date of Patent: Feb. 25, 2020

(54) MICROFLUIDIC SORTING DEVICE

(71) Applicant: European Molecular Biology Laboratory, Heidelberg (DE)

(72) Inventors: Christoph Merten, Heidelberg (DE); Qingzong Tseng, Heidelberg (DE); Ramesh Utharala, Miryalaguda (IN); Lukas Frese, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 213 days.

(21) Appl. No.: 15/561,404

(22) PCT Filed: Mar. 24, 2016

(86) PCT No.: PCT/EP2016/056637
§ 371 (c)(1),
(2) Date: Sep. 25, 2017

(87) PCT Pub. No.: WO2016/151107
PCT Pub. Date: Sep. 29, 2016

(65) Prior Publication Data
US 2018/0104691 A1 Apr. 19, 2018

(30) Foreign Application Priority Data
Mar. 24, 2015 (EP) .................................. 15160580

(51) Int. Cl.
*B01L 3/00* (2006.01)
*G01N 15/10* (2006.01)
*G01N 15/14* (2006.01)

(52) U.S. Cl.
CPC ... *B01L 3/502738* (2013.01); *B01L 3/502761* (2013.01); *G01N 15/1425* (2013.01);
(Continued)

(58) Field of Classification Search
CPC ...... B01L 2200/0652; B01L 2300/0816; B01L 2400/0481; B01L 2400/0655;
(Continued)

(56) References Cited

U.S. PATENT DOCUMENTS

2003/0175980 A1* 9/2003 Hayenga ........... B01L 3/502738
436/63
2007/0243627 A1* 10/2007 Takayama ......... B01L 3/502715
436/180
(Continued)

OTHER PUBLICATIONS

Fulwyler, M.J. "Electronic separation of biological cells by volume," Science, Nov. 12, 1965; 15 150(3698):910-911.
(Continued)

*Primary Examiner* — Jennifer Wecker
(74) *Attorney, Agent, or Firm* — 24IP Law Group USA, PLLC; Timothy Dewitt

(57) ABSTRACT

A sorting device (10) is disclosed comprising a channel (40) adapted to allow passage of a plurality of samples in a fluid to a first side of a sorting junction (50) and a plurality of Braille valves (105) connected by a plurality of connectors to the sorting junction (50). An analysis device (80), such as a camera, is used for analysing ones of the plurality of the samples and adapted to control ones of the plurality of Braille valves depending on properties of the analysed ones of the plurality of the samples.

14 Claims, 7 Drawing Sheets

(52) U.S. Cl.
CPC .. *G01N 15/1484* (2013.01); *B01L 2200/0652* (2013.01); *B01L 2300/0816* (2013.01); *B01L 2400/0481* (2013.01); *B01L 2400/0655* (2013.01); *G01N 2015/1006* (2013.01); *G01N 2015/149* (2013.01)

(58) Field of Classification Search
CPC ......... B01L 3/502738; B01L 3/502761; G01N 15/1425; G01N 15/1484; G01N 2015/1006; G01N 2015/149
See application file for complete search history.

(56) References Cited

U.S. PATENT DOCUMENTS

| | | | | |
|---|---|---|---|---|
| 2007/0248958 | A1* | 10/2007 | Jovanovich | B01F 11/0071 435/6.19 |
| 2008/0124726 | A1* | 5/2008 | Monforte | B01L 3/502784 435/6.12 |
| 2008/0124779 | A1* | 5/2008 | Oh | B01L 3/502761 435/173.9 |
| 2008/0135114 | A1 | 6/2008 | Takayama et al. | |
| 2016/0016169 | A1* | 1/2016 | Ben-Yakar | B01L 3/502738 506/26 |
| 2017/0234795 | A1* | 8/2017 | Issadore | G01N 21/6428 436/172 |

OTHER PUBLICATIONS

Abate AR, Agresti JJ, Weitz DA, "Microfluidic sorting with high-speed 30 single-layer membrane valves," Applied physics letters. May 17, 2010; 96(20).

Fu AY, Spence C, Scherer A, Arnold FH, Quake SR, "A microfabricated fluorescence-activated cell sorter," Nat. Biotechnol. Nov. 1999; 17(11):1109-1111.

El Debs B, Utharala R, Balyasnikova IV, Griffiths AD, Merten CA, "Functional single-cell hybridoma screening using droplet-based microfluidics," Proc 30 Natl Acad Sci U S A. Jul. 17, 2012; 109(29):11570-11575.

Gu W, Zhu X, Futai N, Cho BS, Takayama S., "Computerized microfluidic cell culture using elastomeric channels and Braille displays," Proc Natl Acad Sci USA, Nov. 9, 2004;101(45):15861-15866.

Tung YC, Torisawa YS, Futai N, Takayama S, "Small volume low mechanical stress cytometry using computer-controlled Braille display microfluidics," Lab on a Chip. 2007; 7(11):1497-1503.

Fu AY, Chou HP, Spence C, Arnold FH, Quake SR, "An integrated microfabricated cell sorter," Anal Chem. Jun. 1, 2002; 74(11):2451-2457.

* cited by examiner

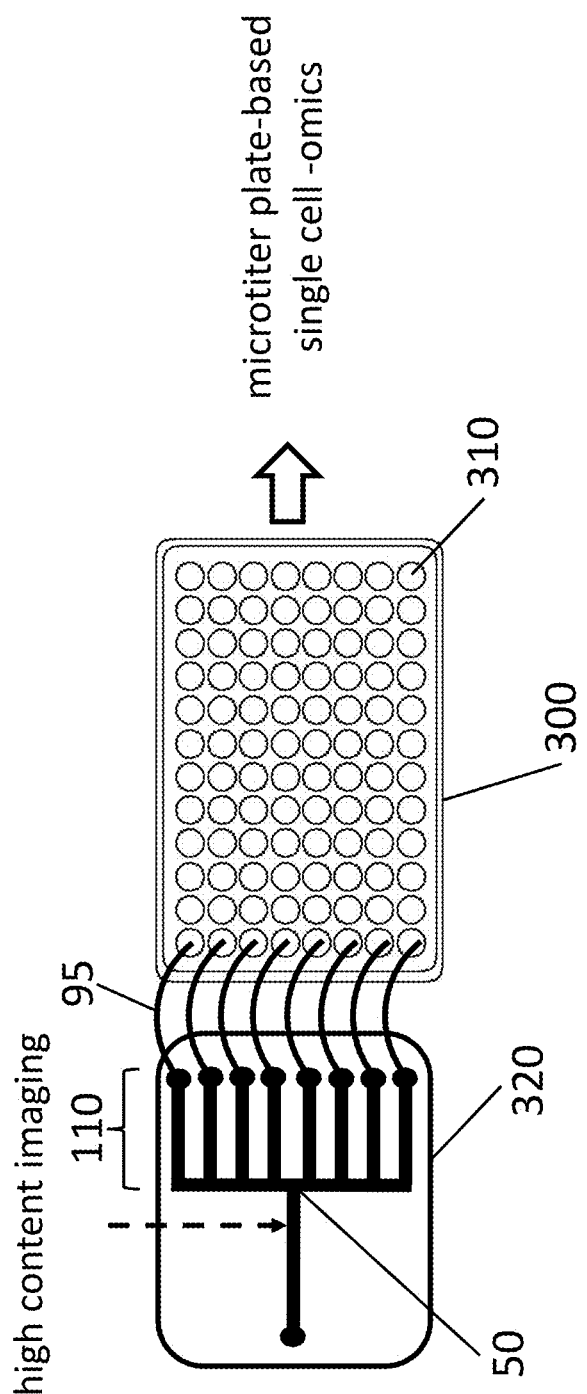

MICROFLUIDIC SORTING DEVICE

CROSS-REFERENCE TO RELATED APPLICATIONS

This patent application claims priority and benefit of European patent application No 15 160 580.5 filed on 24 Mar. 2015.

FIELD OF THE INVENTION

The invention relates to a sorting device

BACKGROUND OF THE INVENTION

Active cell sorting has been developed almost five decades ago (see Fulwyler M. J. "Electronic separation of biological cells by volume," Science, Nov. 12, 1965; 150 (3698):910-911). The fields of use for the active cell sorting have increased since the first publication. This increase has resulted in annual sales of cell separation/cell isolation products of $2.5 billion in 2014 (www.marketsandmarkets.com/PressRelease/cell-isolation.asp, downloaded on 25 Feb. 2015).

Modern fluorescence-activated cell sorters have a throughput of several 10,000 cells per second. However, these cell sorters are quite expensive (more than 200,000 US$ per device) and are not suited for the sorting of very small amounts of cell material (e.g. from patient biopsies or other primary cells). Furthermore, the size of objects to be sorted is limited. For example, different nozzles are required when sorting different cells or multicellular organisms.

Prior art cell microfluidic sorters use pneumatically operated valves, as is known from Abate A R, Agresti J J, Weitz D A. Microfluidic sorting with high-speed single-layer membrane valves. Applied physics letters. May 17, 2010; 96(20), Fu A Y, Spence C, Scherer A, Arnold F H, Quake S R. A microfabricated fluorescence-activated cell sorter. Nat Biotechnol. November 1999; 17(11):1109-1111, and Fu A Y, Chou H P, Spence C, Arnold F H, Quake S R. An integrated microfabricated cell sorter. Anal Chem. Jun. 1, 2002; 74(11): 2451-2457.

The use of these pneumatically operated valves is quite expensive as the control units including macroscopic solenoid valves typically cost around 25,000 US$ (for example from Fluigent).

SUMMARY OF THE INVENTION

The sorting device described herein is an inexpensive standalone device, which costs less than 3,500 US$. The sorting device is capable of sorting samples, such as cells, multicellular organisms and microfluidic droplets. This sorting device has many fields of applications, such as but not limited to cell separation of primary tissue samples (e.g. from patient biopsies, blood samples, primary tissues) or phenotype-dependent sorting of individual cells for correlating phenotypes and genotypes of heterogeneous populations.

The sorting device uses a Braille display to control a plurality of Braille valves to sort the samples in the sorting device. The use of the Braille valves is significantly cheaper (less than 1,000 US$) and more compact than prior art valves. Furthermore, the use of the Braille valves enables the use of single-layer microfluidic chips for the sorting device.

Braille displays have been used previously to actuate microfluidic chips for cell analysis (similar to a FACS analyzer), see Tung Y C, Torisawa Y S, Futai N, Takayama S. "Small volume low mechanical stress cytometry using computer-controlled Braille display microfluidics", Lab on a Chip. 2007; 7(11):1497-1503. The use of the Braille display for sorting of samples such as cells, droplets or multicellular embryos has not been reported in the literature.

The sorting device of this document comprises a channel, which is adapted to allow passage of a plurality of samples in a fluid to a first side of a sorting junction and a plurality of the Braille valves connected by a plurality of connectors to the sorting junction. The sorting device includes further an imaging device for imaging ones of the plurality of the samples and adapted to control ones of the plurality of the Braille valves depending on properties of the imaged ones of the plurality of the samples.

The sorting junction and the plurality of Braille valves can be located on two different microfluidic chips connected by tubing. This allows a great degree of flexibility, as one of the microfluidic chips can be re-used whilst the other one of the microfluidic chips is changed.

In one aspect, the sorting device further comprises a microtiter plate having wells that are fluidly connected to connections controllable by at least one of the Braille valves. The wells collect similar ones of the samples based on the properties of the samples.

At least part of the sorting device can be made from a compressible or expandable polymer which enables the channel to expand to accept temporarily more of the fluid if all of the plurality of Braille valves are closed.

A method of sorting a plurality of samples in a fluid in the channel is also disclosed. The method comprises flowing the fluid with the plurality of samples along the channel and analysing ones of the plurality of samples to generate a sample image. The samples are analysed to determine at least one property of the sample and one of a plurality of Braille valves is opened, whereby the opened one of the plurality Braille valves is dependent on the properties of the sampled image. The opening of the Braille valve allows the analysed sample to enter one of a plurality of collection channels connected with the opened one of the Braille valve. Examples of the analysis include, but are not limited to, imaging or spectroscopy.

The method also enables pausing of the flow of the fluid during the imaging of the sample. This pausing enables better classification of the samples, as blur is reduced when, for example, making images of the samples for analysis of the samples.

DESCRIPTION OF THE FIGURES

FIG. 3 shows an actual example of sorting device connected to a microtiter plate.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

A microfluidic sorting device 10 is described. The sorting device 10 is capable of sorting samples comprising objects, which have a large size range. This size range of the objects can be from a few micrometers to several hundred micrometers in diameter. The sorting device 10 is also capable of sorting small amounts of the samples and can thus be used in the sorting of rare cells or in applications in which only a small amount of the samples are available. The sorting device 10 also enables the sorting of microfluidic droplets, which enables screening of antibodies and other (bio)molecules, see for example El Debs B, Utharala R, Balyasnikova I V, Griffiths A D, Merten C A. Functional single-cell hybridoma screening using droplet-based microfluidics. Proc Natl Acad Sci USA. Jul. 17, 2012; 109(29):11570-11575.

Figure 1A:
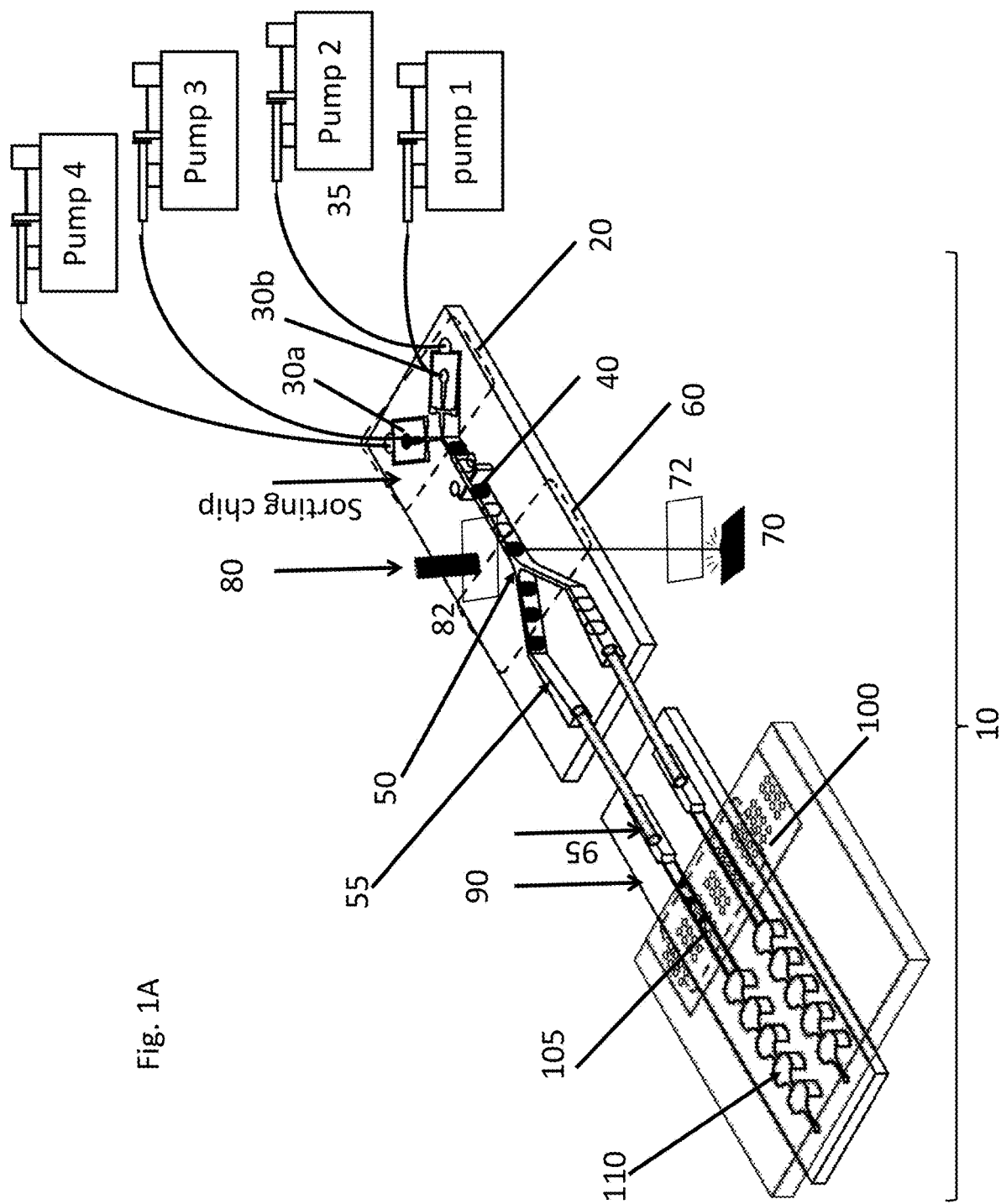
FIGS. 1A and 1B show an example of the sorting device in a first embodiment and a second modified embodiment.
Figure 1B:
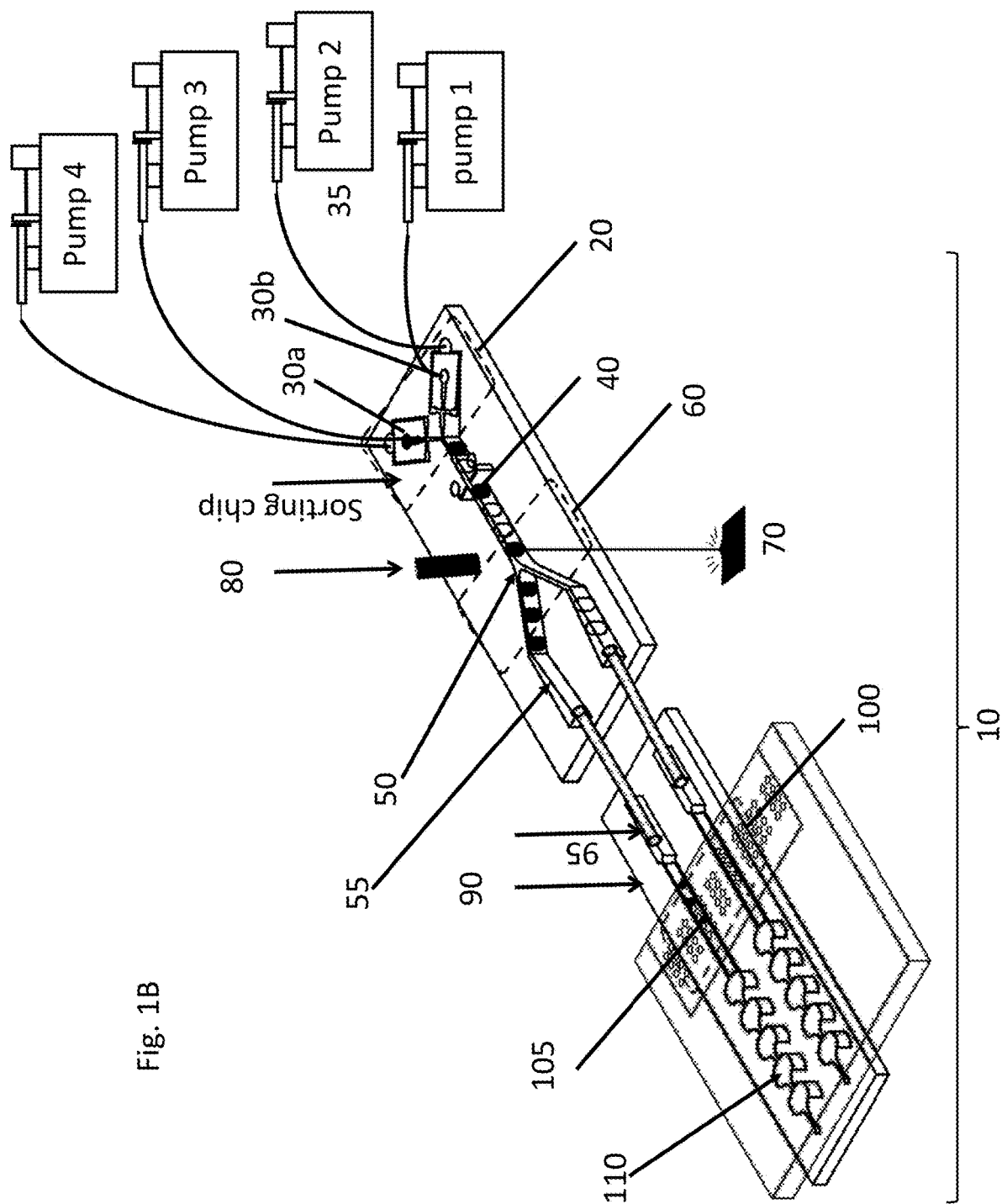

FIG. 1 shows a first aspect of the sorting device 10. The samples, comprising for example, droplets, cells or even multicellular embryos as the objects are loaded through a first inlet 30a and a second inlet 30b in the first section 20 of the sorting device 10. The loaded samples flow or pass along a channel 40 to a sorting junction 50 in a second section of the sorting device 10. The channel 40 is typically around 50 µm in depth and several hundred µm in width. The channel 40 can be several millimetres long. These dimensions of the channel 40 are not, however, limiting of the invention.

An LED light source 70, mounted below the sorting junction, shines a light beam at the sorting junction 50. A camera 80 mounted above the sorting device 10 takes an image of the samples at the sorting junction and a computing device (not shown) processes the image of the samples to determine one or more properties. The computing device analyses the image and a sorting decision is made based on the determined property as a sorting criteria. The analysis is done in one aspect by analysing the colours of the drops in the channel 40 crossing a line perpendicular to the channel 40. Other analyses could be carried out by measuring the size and shapes of objects in the drops in the channel 40 and/or reviewing the contents of the drops. The sorting device 10 is made in one aspect of the invention from polydimethylsiloxane (PMDS). It would be also possible to carry out laser fluorescence spectroscopy on the objects in the drops at the sorting junction 50 to determine the properties used as the sorting criteria. In this case the intensity of the fluorescence from the samples can be measured using a photomultiplier tube in place of the camera 80 as the analysis device.

The sorting is implemented by opening or closing a plurality of Braille valves comprising a channel and a pin (the channel above the pin is indicated as circle 105) in the third section 100 of the sorting device 10, which is located further downstream of the sorting junction 50. The Braille valves 105 are shown in this aspect as being mounted on a separate microfluidic valve chip 90, which is connected by tubing 95 to the sorting junction 50. The diameter of the tubing 95 would be typically less than 1 mm, but its length could be from around a centimeter to up to a meter in length. The third section 100 has a plurality of collection channels 110, but only two of the collection channels 110 are illustrated here for simplicity. The collection channels 110 will have a depth of less than 1 mm and be several hundred micrometers wide with a length in the millimeter region.

The microfluidic chip of the third section 100 of the sorting device 10 is a different microfluidic chip than that for the first section 20 and the second section 60 to allow a greater degree of flexibility. The first section 20, the second section 60 and the third section 100 could be located on a single microfluidic chip. The first section 20 and the second section 60 can be changed for different applications if they are located on a different microfluidic chip whilst the third section with the collection channels 100 and the Braille valves 105 can be re-used.

Figure 5:
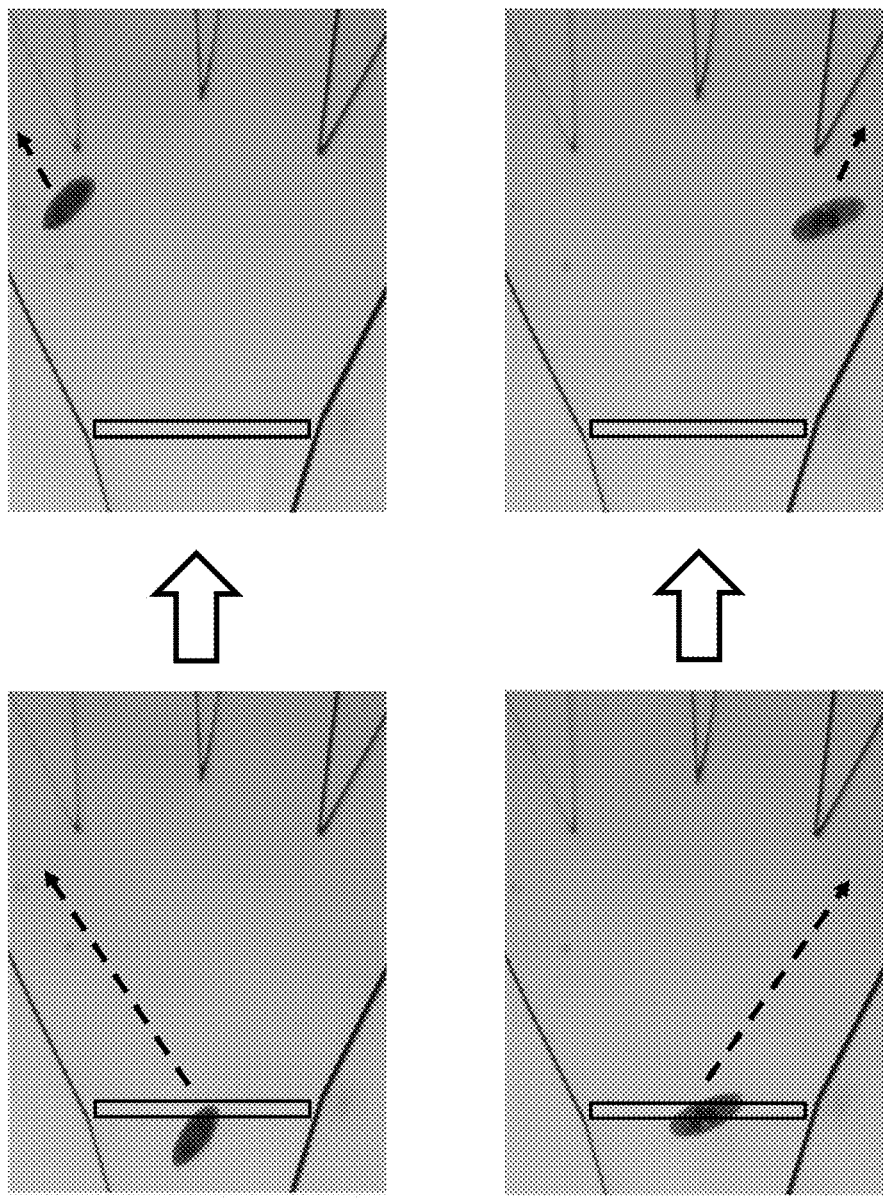
FIG. 5 shows sorted *Drosophila* embryos.

FIG. 5 shows an image of *Drosophila* embryos in the channel 40 taken at the sorting junction 50. The *Drosophila* embryos can be sorted according to one of their properties. In this example, the property used for sorting is their fluorescence detected in camera 80.

The microfluidic Braille valves 105 are known, for example, from the publications Gu W, Zhu X, Futai N, Cho B S, Takayama S. Computerized microfluidic cell culture using elastomeric channels and Braille displays. Proc Natl Acad Sci USA. Nov. 9, 2004; 101(45):15861-15866 and Tung Y C, Torisawa Y S, Futai N, Takayama S. Small volume low mechanical stress cytometry using computer-controlled Braille display microfluidics. Lab on a Chip. 2007; 7(11):1497-1503. The microfluidic Braille valves can be used as the Braille valves 105 in the sorting device 10. These Braille valves 105 are operated by a Braille display (schematically shown below the chip in the third section 100 of FIG. 1) and have a response time of around 30 ms. This allows a potential throughput of up to ~30 Hz.

In one aspect, the microfluidic device 10 possesses sixty-four Braille valves 105, but this is not limiting of the invention. The samples in the microfluidic device 10 are sorted into multiple different ones of the collection channels 110 according to their sorting criteria, such as the phenotype of the objects in the samples. Further examples of properties as the sorting criteria include, but are not limited to, fluorescence intensities, different colours, different sizes and different morphologies.

The sorting decision is based in this example on data obtained from the images made at the sorting junction 50. The sorting device 10 can, in one example, measure the RGB intensities of the samples flowing in the channel 40.

In one aspect of the sorting device 10, the Braille valves 105 enable stopping the flow of the samples for, e.g. 1 second, through the sorting junction 50 during acquisition of the image by the camera 80. This stopping enables more complex readouts of the data from the image to determine the properties, such as high content confocal imaging, which can be implemented without blurring of the samples in the image.

Figure 2A:
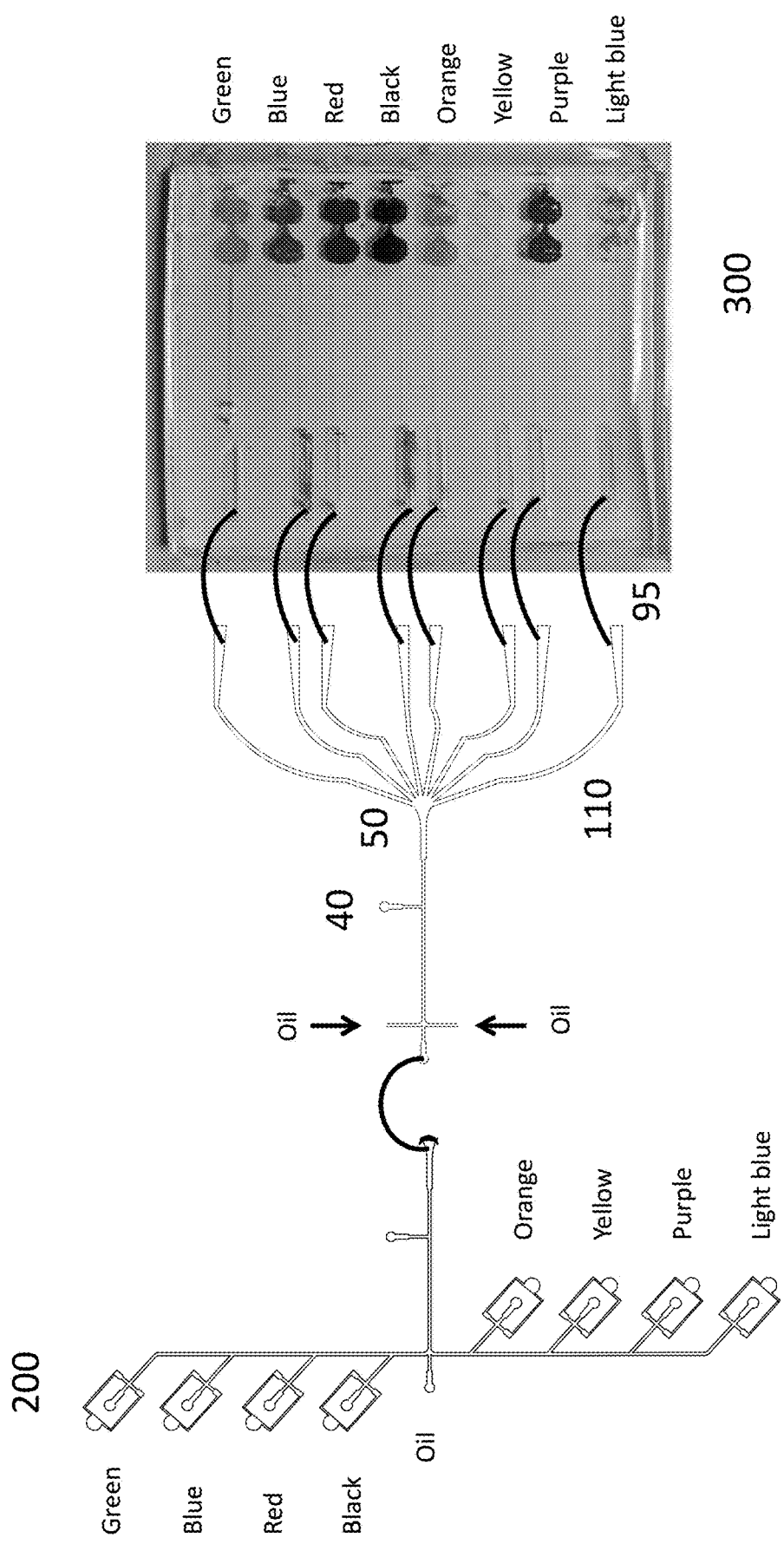
FIG. 2A shows a theoretical example of the use of the sorting device.

One example of the use of the sorting device 10 is shown in FIG. 2A, which illustrates schematically multiway sorting of coloured droplets as sample. The sorting device 10 of FIG. 2A is connected via the tubing 95 to eight drop makers 200, similar to those described in El Debs B, Utharala R, Balyasnikova I V, Griffiths A D, Merten C A. Functional single-cell hybridoma screening using droplet-based microfluidics. Proc Natl Acad Sci USA. Jul. 17, 2012; 109(29): 11570-11575.

The drop makers 200 producing the coloured droplets of the samples. The droplets are encapsulated by surrounding the droplets with an immiscible oil. The colour of the samples is due to aqueous dyes that are of a different colour. The drop makers 200 are connected upstream through the channel 40 or an additional tubing to the sorting junction 50.

The droplets in the channel 40 only come together after encapsulation, i.e. there are no mixing of the aqueous dyes in the channel 40.

Let us suppose that, at the sorting junction 50, the droplets from the channel 40 pass through the sorting junction 50 in a random order (in terms of their colours). The image is taken by the camera (80—not shown on FIG. 2) and the sorting decision is made based on the RGB value of the droplet containing the coloured sample. This allows collecting pure populations of droplets of samples of a specific colour in the downstream collection channels 110.

Figure 2B:
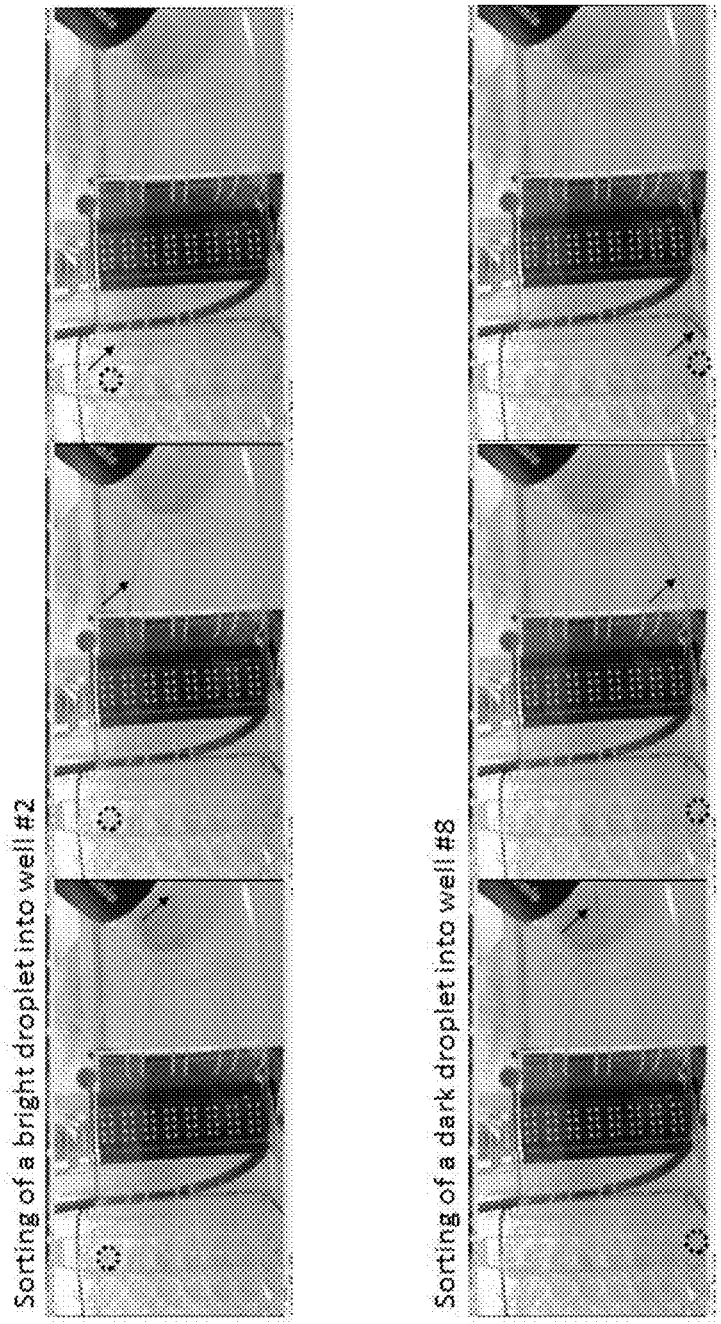
FIG. 2B shows an actual example of the use of the sorting device.

An actual example of the use of the sorting device 10 is shown in FIG. 2B The sorting of individual droplets is indicated by arrows into wells of a microtiter plate. The topmost set of images shows the sorting of a bright droplet into a target well no 2 and the bottommost set of images shows the sorting of a dark droplet into a target well no 8. In each case, the target well is indicated by a dashed circle in the images. Upon detection of one of the droplets, the target well for the droplet is determined and the Braille valves for this specific fluidic connection is kept open until the droplet has passed the entire way from the sorting module to the microtiter plate. It is possible to fill more than eight wells by simply moving the tube adapter (aligning the ends of all tubing 95 with the wells of the microtiter plate; part on the left side of each image) to the next column of the wells.

One issue for the use of the Braille valves 105 in the past for sorting applications is the fact that the valve part of the chip is covered by a Braille display. This has made imaging of the samples very difficult. The sorting junction 50 of the sorting device 10 is observable under the camera 80 (or a microscope or with a photomultiplier tube). The sorting device 10 has the Braille valves 105 in a different third section 100 separated from the second section 60 with the sorting junction 50 and therefore not in the same field of view as the camera 80.

The Braille valves 105 are located downstream of the sorting junction 50 at a distance of at least 3000 µm, in this example. The Braille values 105 could be either on the same microfluidic chip as the sorting junction 50 or on a second microfluidic chip connected by the tubing 95 as shown in FIG. 1.

The fluids containing the samples are injected by external pumps 35 (e.g. computer controlled syringe pumps, pressure driven flow controllers, electro-osmotic pumps, etc.) in the sorting device system, rather than using previously described peristaltic motion of the Braille pins themselves. This allows stable flow of the samples through the channel 40 and the tubing 95, without significant pulsing effects and still enables the stopping of the fluid flow with the samples temporarily during the image acquisition. The PDMS from which the sorting device 10 is made has a degree of flexibility and thus the fluids can be continuously injected, even when all of the Braille valves 105 are closed. As long as this closure lasts no longer than a few seconds, increasing pressure in the channels 40 is tolerated by the expanding PDMS. It will be appreciated that PDMS is only one type of flexible polymer, from which the channels 40 are made, and that other types of flexible polymers could be used.

The Braille display allows multi-way sorting, as is shown with reference to FIG. 2. It should be possible to sort individual ones of the cells in the samples in the fluid directly into different wells 310 of a microtiter plate 300. This is of interest for single cell genomics. Using prior art methods, it is difficult to first detect the phenotype of an individual rare cell in the fluid, perform a sequencing step on the rare cell and then correlate the phenotype with the genotype.

It has been found that in prior art single cell genomics platforms (such as the Fluidigm C1 platform) the cells in the fluid are trapped at random positions in the sequencing chip and many of the cells even end up in waste without being trapped. Hence sequencing data obtained from the cells cannot be assigned to a particular phenotype determined further upstream.

The sorting device 10 overcomes this problem by outputting the cells sorted on the microfluidic chip 320 individually into the wells 310 of the microtiter plate 300. The current implementation involves an 8-way sorting procedure in which each of the eight collection channels 110 are controlled by one of the Braille valves 105. The Braille display itself has a total of 64 pins in this example (and even bigger ones are in principle available) thus allowing the scaling of up to 64 collection channels 110 from which the individual cells can be flushed into different ones of the wells 310 on the microtiter plate 300 on demand.

Once this flushing has been done, the tubing 95 connecting the sorting device 10 on the microfluidic chip 320 and the microtiter plate 300 are moved to the next 64 wells (e.g. of a 384-well plate) or simply connected to the next microtiter plate (not shown). An overall throughput of at least 64 cells within 5 min can be implemented (equalling more than 6000 sorted samples per day). All of the downstream-omics procedures can then be carried out in a highly parallelized fashion (having free access to each individual cell).

An example of the sorted organisms is shown in FIG. 5, which shows positively and negatively sorted *Drosophila* embryos.

Figure 4:
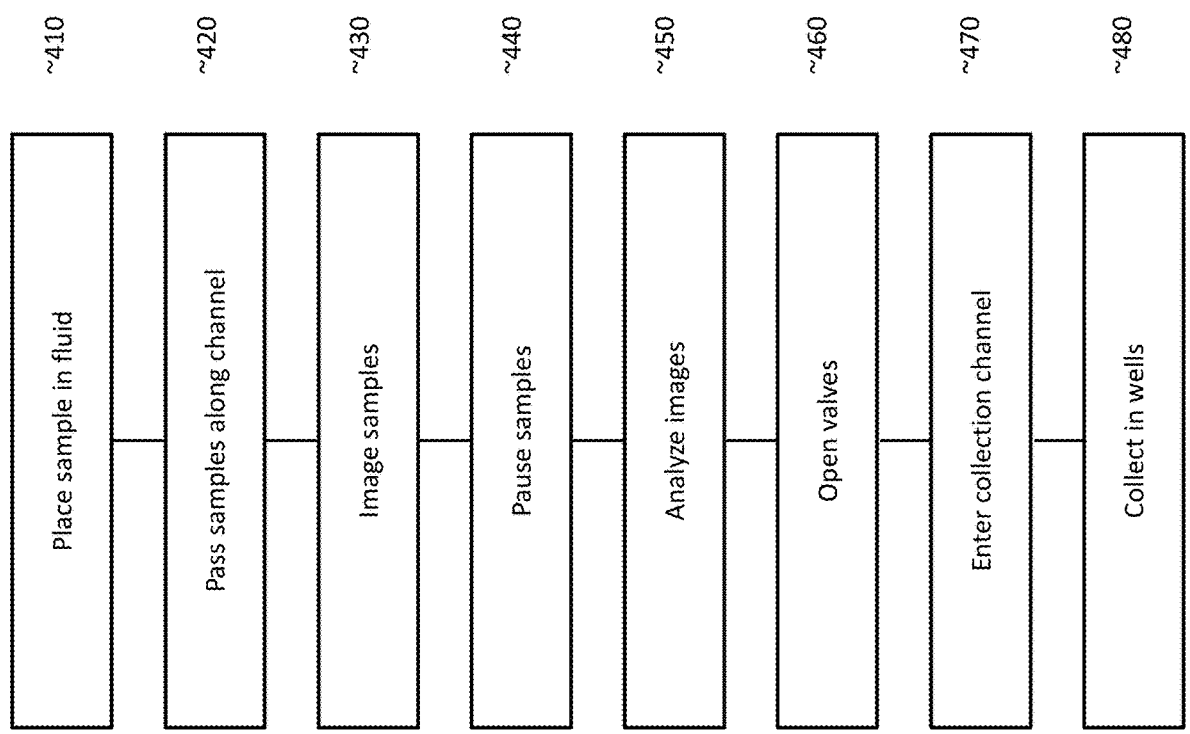
FIG. 4 shows an example of the method.

FIG. 4 shows an outline of the method of this sorting device. In a first step 410, a plurality of samples is placed in a fluid in the channel 40. The fluid is injected into the channel 40 and caused to pass along the channel 40 in step 420 to a sorting junction 50, at which the samples are imaged in step 430. The fluid can be paused at the sorting junction 50 if required, as seen in step 440. The images taken from the samples in step 430 are analysed in step 450 and, based on the properties of the samples, one of the Braille valves 105 is opened in step 460. The opening of the Braille valve in step 460 causes the fluid with the sample to enter into one of the collection channels 100 in step 470, from which the sample can move through the collection channel 100 to one of the wells 310 where the sample(s) are collected in step 480. This method has been described in connection with the imaging of the samples. It is equally applicable when other analyses of the sample are carried out, in which case the steps 430 and 450 are replaced by appropriate steps for the other analyses.

REFERENCES

1. Fulwyler M J. Electronic separation of biological cells by volume. Science. Nov. 12, 1965; 150(3698):910-911.
2. El Debs B, Utharala R, Balyasnikova I V, Griffiths A D, Merten C A. Functional single-cell hybridoma screening using droplet-based microfluidics. Proc Natl Acad Sci USA. Jul. 17, 2012; 109(29):11570-11575.
3. Gu W, Zhu X, Futai N, Cho B S, Takayama S. Computerized microfluidic cell culture using elastomeric channels and Braille displays. Proc Natl Acad Sci USA. Nov. 9, 2004; 101(45):15861-15866.

4. Tung Y C, Torisawa Y S, Futai N, Takayama S. Small volume low mechanical stress cytometry using computer-controlled Braille display microfluidics. Lab on a Chip. 2007; 7(11):1497-1503.
5. Abate A R, Agresti J J, Weitz D A. Microfluidic sorting with high-speed single-layer membrane valves. Applied physics letters. May 17, 2010; 96(20).
6. Fu A Y, Spence C, Scherer A, Arnold F H, Quake S R. A microfabricated fluorescence-activated cell sorter. Nat Biotechnol. November 1999; 17(11):1109-1111.
7. Fu A Y, Chou H P, Spence C, Arnold F H, Quake S R. An integrated microfabricated cell sorter. Anal Chem. Jun. 1, 2002; 74(11):2451-2457.

REFERENCE NUMERALS

10 Sorting device
20 First section
30a, b Inlets
40 Channel
50 Sorting junction
60 Second section
70 LED light source
80 Camera
90 Valve chip
95 Tubing
100 Third section
105 Braille valves
110 Collection channel
200 Drop makers
300 Microtiter plate
310 Wells
320 Microfluidic chip

The invention claimed is:

1. A sorting device comprising:
 a channel adapted to allow passage of a plurality of samples in a fluid to a first side of a sorting junction;
 a plurality of Braille valves connected by a plurality of connectors to the sorting junction and located downstream at a distance to the sorting junction;
 an analysis device mounted at the sorting junction for analysing ones of the plurality of the samples and adapted to control ones of the plurality of Braille valves depending on properties of the analysed ones of the plurality of the samples.

2. The sorting device of claim 1, in which the sorting junction and ones of the Braille valves are separated by at least 3000 μm.

3. The sorting device of claim 1 in which the sorting junction and the plurality of Braille valves are on located on two different microfluidic chips connected by tubing.

4. The sorting device of claim 1, in which the fluid is injected by external pumps.

5. The sorting device of claim 1, further comprising a microtiter plate having wells fluidly connected to connections controllable by at least one of the Braille valves.

6. The sorting device of claim 1, wherein at least parts of the sorting device are made of a compressible or expandable polymer.

7. The sorting device of claim 1, wherein the analysis device is one of a camera, a microscope or a photomultiplier tube.

8. The sorting device of claim 1, wherein the channel is made of a flexible polymer.

9. A method of sorting a plurality of samples in a fluid in a channel comprising:
 passing the fluid with the plurality of samples along the channel;
 analysing at a sorting junction ones of the plurality of samples to determine at least one property of one of the samples;
 opening one of a plurality of Braille valves, the opened one of the plurality Braille valves, located downstream at a distance to the sorting junction, being dependent on the at least one property; and
 allowing the analysed sample to enter one of a plurality of collection channels being connected with the opened one of the Braille valve.

10. The method of claim 9, further comprising pausing flow of the fluid during the analysis of the sample.

11. The method of claim 9, further comprising injecting the fluid into the channel.

12. The method of claim 11, further comprising closing all of the plurality of Braille valves whilst still injecting the fluid into the channel.

13. The method of claim 9, further comprising passing a plurality of the analysed samples having similar properties along a same one of the plurality of collection channels.

14. The method of claim 9, wherein the analysing of ones of the samples comprising imaging the sample and analysing the images of the sample.

* * * * *